United States Patent [19]

Weinstock

[11] 4,192,872

[45] Mar. 11, 1980

[54] 6-HALO-3-LOWER ALKYL-7,8-DIHYDROXY-1-PHENYL-2,3,4,5-TETRAHYDRO-1H-3-BENZAZEPINES

[75] Inventor: Joseph Weinstock, Phoenixville, Pa.

[73] Assignee: SmithKline Corporation, Philadelphia, Pa.

[21] Appl. No.: 892,063

[22] Filed: Mar. 31, 1978

Related U.S. Application Data

[63] Continuation-in-part of Ser. No. 742,965, Nov. 17, 1976, Pat. No. 4,160,765.

[30] Foreign Application Priority Data

Oct. 4, 1977 [ZA] South Africa .................. 77/5910

[51] Int. Cl.$^2$ .................. A61K 31/55; C07D 223/16
[52] U.S. Cl. .................. 424/244; 260/239 BB
[58] Field of Search .................. 260/239 BB; 424/244

[56] References Cited

U.S. PATENT DOCUMENTS

| | | | |
|---|---|---|---|
| 3,496,166 | 2/1970 | Mull et al. | 260/239 BB |
| 3,988,339 | 10/1976 | Kaiser et al. | 424/258 |

FOREIGN PATENT DOCUMENTS

| | | | |
|---|---|---|---|
| 77/5910 | 10/1977 | South Africa. | |
| 500194 | 1/1971 | Switzerland | 260/239 BB |
| 555831 | 11/1974 | Switzerland | 260/239 BB |
| 1225053 | 3/1971 | United Kingdom | 260/239 BB |

*Primary Examiner*—Donald G. Daus
*Assistant Examiner*—D. B. Springer
*Attorney, Agent, or Firm*—William H. Edgerton

[57] ABSTRACT

6-Halo-7,8-dihydroxy-1-phenyl-2,3,4,5-tetrahydro-1H-3-benzazepines whose structures have a lower alkyl substituted at the 3 or N-position have potent and often specific anti-Parkinsonism activity by means of their central dopaminergic effect. The lead compound of the series is 6-chloro-3-methyl-1-phenyl-7,8-dihydroxy-2,3,4,5-tetrahydro-1H-3-benzazepine as the base or its salts such as the hydrochloride, hydrobromide or methane sulfonate.

14 Claims, No Drawings

6-HALO-3-LOWER ALKYL-7,8-DIHYDROXY-1-PHENYL-2,3,4,5-TETRAHYDRO-1H-3-BENZAZEPINES

This application is a continuation-in-part application of copending Ser. No. 742,965 filed Nov. 17, 1976, now U.S. Pat. No. 4,160,765 issued July 10, 1979.

This invention concerns a group of compounds whose structures have a 1-phenyl-2,3,4,5-tetrahydro-1H-3-benzazepine skeleton specifically substituted with hydroxy groups at the 7,8-positions, a halo group at the 6-position and a lower alkyl group at position 3. These new compounds are unique dopaminergic agents having a powerful agonist effect at dopaminergic sites within the central nervous system.

STATEMENT OF THE PRIOR ART

Certain 1-phenyl-2,3,4,5-tetrahydro-1H-3-benzazepines have been described in U.S. Pat. Nos. 3,609,138, 3,743,731, 3,393,192, 4,011,319 and 4,052,506; British Pat. 1,118,688; and Swiss Pat. No. 555,831, including general methods of preparation. However these references disclose no specific benz- trisubstituted compounds, no specific 6-substituted 1-phenylbenzazepine compounds of any kind of no particular advantage to a combination of 6-halo and 3-lower alkyl substitution in the structures. British Pat. No. 1,225,053 discloses certain halo-substituted benzazepines not related in structure to those claimed here.

DESCRIPTION OF THE INVENTION

This invention offers a new group of compounds which are 1-phenyl-2,3,4,5-tetrahydro-1H-3-benzazepines having (a) at least three specific substituents in the benz-ring of the nucleus, one of which is a halo or halo-containing group substituted at the 6-position the other two are hydroxy or derivatized hydroxy groups at the 7 and 8-positions, and (b) a lower alkyl substituent at the 3 or N-position. These compounds have utility as medicinally active compounds especially as anti-Parkinsonism agents due to their potent central nervous system dopaminergic activity. They also demonstrate little activity in animal models which are known to test for activity at peripheral dopamine receptors. Generally speaking therefore they have unique anti-Parkinsonism activity due to a potent dopaminergic mechanism of action, especially within the central nervous system.

The structures of the compounds of this invention are specifically identified by having a halo, that is, a chloro, bromo, iodo or fluoro or halo-containing substituent such as a trifluoromethyl or trifluoroethyl group at the 6-position of the 1-phenyltetrahydro-3-benzazepine system coupled with a 3-lower alkyl group. Exemplary of this new group of compounds are those represented by the following structural formulas:

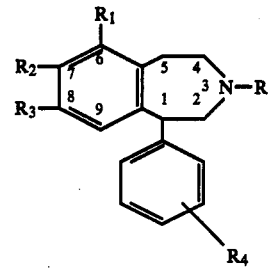

wherein:
R is methyl, ethyl or allyl;
$R_1$ is halo or trifluoromethyl;
$R_2$ and $R_3$ are hydroxy or derivatized hydroxy especially a lower alkanoyloxy of 2–7 carbon atoms such as acetoxy; and
$R_4$ is hydrogen, methyl, halo such as chloro, bromo or fluoro, methoxy or trifluoromethyl.

The preferred compounds of this invention have the basic structural formula:

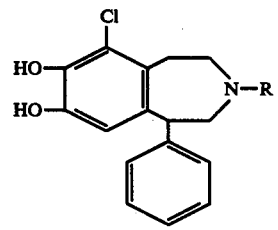

in which R is ethyl or advantageously methyl. These include salts, esters or any other derivatives or metabolic products which owe their biological activity to the basic compounds of Formula II. Such compounds may contain acetoxy, isobutyryloxy, butyryloxy, isoamyloxy and such groups which are metabolized in the body to release the active dihydroxy parent of Formula II.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bis-methylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic and especially methane-sulfonic acid salts are of particular utility.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Specific methods of resolution are disclosed in Swiss Pat. No. 555,831. Unless otherwise specified herein or in the claims, it is intended to include all isomers, whether separated or mixtures thereof. Where isomers are separated, the desired pharmacological activity will usually predominate in one of the isomers. In practice the isomeric mixture is most readily used.

The compounds of Formula I are generally prepared from intermediates of the following formula:

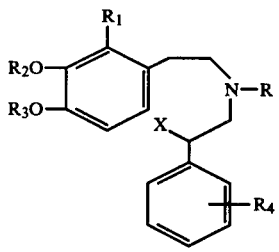

in which X is hydroxyl or its functional equivalent; R is hydrogen or as defined above, $R_1$ and $R_4$ are as defined above; and $R_2$ and $R_3$ are both a lower alkyl especially methyl, benzyl or together are methylene or ethylene; by means of an intramolecular cyclization effected by reaction with a cyclizing agent such as a strong acid for example, trifluoroacetic acid, polyphosphoric acid, sulfuric acid, the preferred sulfuric acid in trifluoroacetic acid, polyphosphoric ester, methanesulfonic acid in methylene chloride or hydrobromic acid or a Lewis acid such as boron trifluoride, aluminum chloride or stannic chloride which generates the desired carbonium ion from the substituent X. The term "chemically inert" means under the conditions of the cyclization reaction the substituent is not altered unless of course the operator so desires. For example carrying out the cyclization in 48% hydrobromic acid when the 7,8-dihydroxy groups are etherified splits the ether links to give the hydroxy cyclic compounds.

The phenethylamines (IV) which are used as starting materials for this method are either known or are prepared by methods described in U.S. Pat. Nos. 3,211,792, 3,804,839, 3,211,792; Chem. Abst. 80, 95398, J. Am. Chem. Soc. 78, 4419 (1956) or in the illustrative examples here disclosed.

When the 3 or N-lower alkyl substituent is absent in the cyclization method described above, it may be conveniently inserted into the structure of the intermediates by alkylation methods known to the art. Most conveniently this reaction is run using the etherified derivatives of the catechol intermediates, for example the 7,8-dimethoxy, 7,8-dibenzyloxy or 7,8-methylenedioxy derivatives. When R at position 3 is methyl, most conveniently a reductive formylation is used such as heating at reflux in formic acid an excess formaldehyde mixture. Other alkylation means can also be used such as using methyl, ethyl or allyl halide in the presence of base such as an alkali metal carbonate or hydroxide in a suitable inert solvent such as dimethylformamide, dimethylacetamide, dimethylsulfoxide or alcohol.

The protective ether groups are then removed such as using 48% hydrogen bromide, boron trichloride, boron tribromide or other conventional ether splitting agents.

To prepare the compounds of Formula I where each of $R_2$ and $R_3$ is alkanoyloxy, the corresponding 3-lower alkyl-dihydroxy-3-benzazepine (obtained by routine N-alkylation of the hydroxyor alkoxybenzazepines) is treated with the appropriate alkanoic acid anhydride or chloride, for example acetic anhydride, to give the desired alkanoyloxy substituted benzazepine. The alkanoyloxy derivatives such as the important O-acetoxy compounds can also be prepared by direct O-acylation of the 6-halo-7,8-dihydroxy-1-phenyl-2,3,4,5-tetrahydro-1H-3-benzazepine hydrobromide in trifluoroacetic acid at ambient temperature with the anhydride or halide followed by N-alkylation.

The intermediates of Formula III above are conveniently prepared by heating equimolar amounts of a styrene oxide with a 3,4-dialkoxyphenethylamine, each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivative from sodium hydride and trimethylsulfonium iodide with the appropriately substituted benzaldehyde.

A preferred method for preparing the phenethanolamine intermediates of Formula III is by condensation of the substituted 3,4-dimethoxyphenethylamine (IV) with a hindered phenylbromohydrin in which the α-hydroxy group is protected by a tert.-butyl or dihydropyranyl moiety.

The compounds of this invention especially those having a halo at position 6 have enhanced dopaminergic activity at central nervous system receptor sites, often in the range of 2–10 times more potent than that of the 3-desalkyl congener. Also the peripheral or cardiovascular dipaminergic effect may be completely suppressed or, at least, diminished. The central dopaminergic activity is manifested by an antiparkinson activity, that is the side effects of Parkinson's disease are ameliorated.

This is demonstrated by employing a modified standard animal pharmacological test procedure reported by Ungerstedt et al., in *Brain Research* 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. The compounds of this invention directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value in mg/kg.

The results following oral administration are expressed similarly as $RD_{1000}$ in mg/kg. This rat rotation test is also described in U.S. Pat. No. 4,052,506 and Advances in Neurology, Vol. 9, 165 (1975).

The test model for peripheral or cardiovascular activity of the compounds is the measure of renal blood flow in anesthetized dogs expressed as $ED_{15}$ in mcg/kg/min following intravenous infusion. This test is described in U.S. Pat. No. 4,011,319 and Gen. Pharmac. 8 1 (1977).

Following are representative test results comparing representative compounds of this invention with those of my parent application as well as with those of the prior art.

TABLE I

R-R4 refer to Formula I.

| No. | Salt | R | $R_1$ | $R_2$ | $R_3$ | $R_4$ | $ED_{15}$ | $RD_{500}$ |
|---|---|---|---|---|---|---|---|---|
| 1. | HCl | H | H | HO | HO | H | 31 | 0.22 |
| 2. | HBr | $CH_3$ | H | HO | HO | H | a. | 0.2 |
| 3. | HBr | $C_2H_5$ | H | HO | HO | H | ina. | 0.59 |
| 4. | HCl | $CH_2CH=CH_2$ | H | HO | HO | H | ina. | 0.1 |
| 5. | HBr | H | Cl | HO | HO | H | 3.5 | 0.3 |
| 6. | HBr | H | Br | HO | HO | H | 9 | 0.27 |
| 7. | HBr | $CH_3$ | Cl | HO | HO | H | ina. | 0.03 |
| 8. | HBr | $C_2H_5$ | Cl | HO | HO | H | 45 | 0.015 |
| 9. | HBr | $C_3H_7$ | Cl | HO | HO | H | ina. | 2. (s.a.) |
| 10. | HBr | $CH_2CH=CH_2$ | Cl | HO | HO | H | 4.5 | 0.03 |
| 11. | HBr | H | Cl | HO | HO | 4-OH | 0.3 | 10 (ina.) |
| 12. | HBr | $CH_3$ | Cl | HO | HO | 3-Cl | ina. | 0.03 |
| 13. | HBr | $CH_2CH=CH_2$ | Cl | HO | HO | 3-Cl | 22 | 0.11 |
| 14. | HCl | $CH_2CH=CH_2$ | Cl | AcO | AcO | H | — | 0.03 |
| 15. | HBr | $CH_3$ | Br | HO | HO | H | — | 0.015 |
| 16. | HBr | $CH_2CH=CH_2$ | Cl | HO | HO | 3-$CH_3$ | — | 0.04 |
| 17. | HBr | $CH_3$ | Cl | HO | HO | 3-$CH_3$ | — | 0.041 |
| 18. | HCl | $CH_3$ | Cl | AcO | AcO | H | — | 0.025 |
| 19. | HBr | $CH_3$ | Cl | HO | H | H | — | 2 (654 ± 307) |

These results demonstrate the critical nature of the 6-halo-7,8-dihydroxy system as well as the lower alkyl substituents at position 3. The 6- and 3'-monotrifluoromethyl congeners have a lower degree of rotation activity. Representative oral activities ($RD_{1000}$) are:

Compound 7-1.94 mgkg; Compound 12-3.29;
Compound 15-2.52; Compound 16-2.9;
Compound 17-2.1; Compound 18-2.22.

Some stereotopy occurred at high oral doses of 5-10 mg/kg when the 3-substituent is other than methyl so high potency is a desirable biological effect.

The pharmaceutical compositions of this invention having central dopaminergic activity are prepared in dosage unit forms by incorporating a compound of Formula I, an isomer or a pharmaceutically acceptable acid addition salt or derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 10 mg to about 400 mg preferably about 50-250 mg of active ingredient per oral dosage unit but this quantity depends on the relative potency of the basic compound, the specific biological activity desired, the route of administration and the conditions of the patient. The ranges given are for oral administration. Parenteral administration would be lower, for example from about 0.5-50 mg per dose.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax. Such sustained release products as well as derivatives which may be gradually metabolised to the active parent can be employed to prolong the antihypertensive activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses within the ranges given above will be administered several times such as from two to five times a day with the daily dosage regimen being selected from about 2 mg to about 1.0 g preferably 50-500 mg/kg. When the method described above is carried out antiparkinson activity is produced.

The following examples are designed solely to illustrate the preparation and use of the compounds of this invention. The temperatures are Centigrade. Other variations of these examples will be obvious to those skilled in the art.

EXAMPLE 1

Isovanillin (200 g, 1.32 mole) was suspended in 1200 cc chloroform. Chlorine (103 g, 1.45 mole) was added by means of 3 500 cc portions of carbon tetrachloride, in which it was dissolved. The suspension was stirred vigorously during the addition and the reaction was kept around 25° by a water bath. The suspension was stirred for 22 minutes after the completion of the addition of chlorine. The precipitate was filtered and crystallized from methanol, then recrystallized from isopropanol/ethyl acetate. Yield 98.7 g (40%, m.p. 204–206°) of 2-chloro-3-hydroxy-4-methoxybenzaldehyde.

The aldehyde product (189.3 g, 1.02 mole) was suspended in 1 l. of dry dimethylformamide, 350 g of potassium carbonate was added. 145 cc (124 g, 1.54 mole) of dimethyl sulfate was added dropwise over a 20 minute period. After the addition the reaction was heated on the steam bath for 5 minutes. 70 cc of water were added and the reaction was again heated for 5 minutes on the steam bath. The mixture was then poured into ice water and the precipitate was collected. It was crystallized from acetic acid/water (800 cc–50 cc). A second crop was obtained from the mother liquor. Yield 180 g (90%) of 2-chloro-3,4-dimethoxybenzaldehyde after drying, m.p. 69°–70°.

The dimethoxybenzaldehyde (180 g, 0.9 mole) was dissolved in 500 cc warm acetic acid. 61 g (0.8 mole) of ammonium acetate was added, followed by 160 cc of nitromethane. The reaction was heated vigorously on the steam bath for 3 hours. Water was then added to the cloud point, while still heating, and the solution was cooled and scratched. The $\beta$-nitrostyrene began to oil out and then crystallized. The solution was cooled. The yellow crystals were collected and dried in a vacuum oven. Yield 175 g (80% m.p. 88°–91°) of 2-chloro-3,4-dimethoxy-$\beta$-nitrostyrene.

The nitrostyrene (80 g, 0.33 mole) was dissolved in 800 cc of dry tetrahydrofuran. Lithium aluminum hydride, as a 3.7 M solution (260 cc, 0.36 mole), was put in a 5 l. 3 neck flask which has been dried and flushed with argon. It was diluted with 500 cc of dry ether. The solution of the nitrostyrene was added in a thin stream. The flask was cooled in an ice bath so that the heat of reaction caused a gentle reflux of the ether. After addition, the reaction was refluxed one hour, then worked up by adding 36 ml of water, 36 cc of 10% sodium hydroxide and 108 ml of water sequentially and carefully, while cooling the reaction in ice.

The precipitate was collected, washed well with ethyl ether and discarded. The ether-tetrahydrofuran mixture was evaporated.

The above reaction was repeated on 83 g of nitrostyrene. The two crude products were combined and distilled at 0.5 mm to collect at 142°–155° the product containing fraction which was pure 2-(2-chloro-3,4-dimethoxyphenyl)ethylamine by t.l.c. (80 g).

The phenethylamine (25.7 g, 0.12 mole) was heated to 115° in an oil bath. Styrene oxide (14.4 g, 0.12 mole) was added and the reaction was heated for 1 hour. After cooling to ~30°, 2:1 petroleum ether/acetone was added to dissolve the oil; N-[(2-hydroxy-2-phenylethyl)]-N-[2-(2'-chloro-3',4'-dimethoxyphenyl)ethyl]amine, crystallized out in 37% yield (15 g) m.p. 100°–101°.

The hydroxyphenethylamine (15 g, (0.445 mole) was dissolved in 60 ml of trifluoroacetic acid and 4.05 ml of concentrated sulfuric acid was added. The reaction was refluxed 2 hours. After cooling most of the trifluoroacetic acid was stripped off and the residue was poured into water. It was made basic with 10% sodium hydroxide and was extracted with ether twice. The ether was dried, and as it was evaporated, a solid separated which was collected; m.p. 115°–121°, 6.0 g of 6-chloro-7,8-dimethoxy-1-phenyl-2,3,4,5-tetrahydro-1H-3-benzazepine.

A solution of 3.7 g of 6-chloro-7,8-dimethoxy-1-phenyl-2,3,4,5-tetrahydro-1H-3-benzazepine in 15 ml of formic acid and 10 ml of formaldehyde is refluxed for 18 hours. The reaction mixture is evaporated to dryness, 20 ml of 6N hydrochloric acid is added and the solution is again evaporated to dryness to give a liquid. The latter is treated with 20 ml of 10% sodium hydroxide solution and the mixture is extracted with ether. The dried extract is evaporated to give 6-chloro-7,8-dimethoxy-3-methyl-1-phenyl-2,3,4,5-tetrahydro-1H-3-benzazepine.

The above prepared 3-methyl benzazepine (2.6 g) is dissolved in 120 ml of dry methylene chloride and 6.8 g (0.027 mol) of boron tribromide is added dropwise at −10°. The resulting solution is warmed at room temperature and stirred for two hours. The excess boron tribromide is destroyed with methanol, added dropwise with ice-cooling. The solution is refluxed on the steam bath to remove hydrogen bromide and then evaporated to dryness to furnish 6-chloro-7,8-dihydroxy-3-methyl-1-phenyl-2,3,4,5-tetrahydro-1H-3-benzazepine hydrobromide, 247°–249°.

The hydrobromide is shaked in a mixture of excess 10% sodium hydroxide and methylene chloride. The organic layer is separated, dried and evaporated to give the desired base. The base is dissolved in methylene chloride and reacted in portions with aliquots containing an excess of methane sulfonic acid, hydrochloric acid, sulfuric acid and acetic acid to give the respective salts.

EXAMPLE 2

7,8-Dimethoxy-1-phenyl-2,3,4,5-tetrahydro-1H-3-benzazepine (280 g, 0.75 mole) was dissolved in 1700 cc of acetic acid. Bromine (280 g, 1.75 mole) was added in a thin stream. The reaction was stirred for two hours. The precipitate, which formed after 1 hour, was collected and washed with ether. It was dissolved in boiling methanol and acetone was added to destroy the bromine excess. 6-Bromo-7,8-dimethoxy-1-phenyl-2,3,4,5-tetrahydro-1H-3-benzazepine hydrobromide was allowed to crystallize from the methanol and a second crop was obtained by adding ether to the mother liquor. Yield 298 g, 77% m.p. 236–238%.

The hydrobromide was shaken in a mixture of excess 10% sodium hydroxide and methylene chloride. The organic layer was separated, dried and evaporated to give a solid base which was crystallized from toluene-hexane; m.p. 125°–128°, yield 238 g (97%).

This 6-bromo-7,8-dimethoxy-1-phenyl-2,3,4,5-tetrahydro-1H-3-benzazepine was methylated and treated with boron tribromide as in Example 1 to give the desired 6-bromo-7,8-dihydroxy-3-methyl-1-phenyl-2,3,4,5-tetrahydro-1H-3-benzazepine hydrobromide, m.p. 181°–183°.

EXAMPLE 3

A mixture of 42.0 g of 57% sodium hydroxide dispersed in oil and 700 ml of dimethyl sulfoxide is stirred at 70°–75° for one to one and one-half hours. The solution is diluted with 700 ml of dry tetrahydrofuran and cooled to 0°, under nitrogen. A 200 g of (1.0 mol) sample of trimethylsulfonium iodide is added in portions, maintaining the temperature between 0°–5°. The mixture is stirred for 15 minutes and then a solution of 70.4 g (0.50 mol) of o-chlorobenzaldehyde in 300 ml of dry tetrahydrofuran is added dropwise. The resulting mixture is stirred at room temperature for four hours, poured into water and extracted with ether. The extract is washed with brine, dried and evaporated in vacuo to leave o-chlorostyrene oxide.

A solution of 27.5 g of N-benzyl-2-chloro-3,4-dimethoxyphenylethylamine and 23.3 g (0.15 mol) of m-chlorostyrene oxide in 500 ml of methanol is stirred and refluxed overnight. The methanol is removed in vacuo and the residual N-benzyl-N-[2-(2-chloro-3,4-dimethoxyphenyl)ethyl]-2-hydroxy-2-(2-chlorophenyl)ethylamine is reduced without further purification. This sample (0.01 mol) is dissolved in ether, acidified with ethereal hydrogen chloride and the hydrochloride precipitates. The latter is dissolved in 90 ml of methanol, the solution is added to a mixture of 0.5 g of palladium-on-charcoal in 10 ml of ethyl acetate and the mixture is hydrogenated at room temperature for 90 minutes at 60 psi. The reaction mixture is filtered and the filtrate evaporated in vacuo to yield N-[2-(2-chloro-3,4-dimethoxyphenyl)ethyl]-2-hydroxy-2-(2-chlorophenyl)ethylamine hydrochloride.

The ethanolamine (0.5 mole) is cyclized in 60 ml of trifluoroacetic acid and 4.5 ml of sulfuric acid, methylated and the protective ether derivatives split as in Example 1 to give 6-chloro-1-(2-chlorophenyl)-7,8-dihydroxy-3-methyl-2,3,4,5-tetrahydro-3H-1-benzazepine and its hydrochloride salt.

EXAMPLE 4

Following the procedure of Example 3 and employing 42.0 g of 57% of sodium hydride in mineral oil, 200 g (0.1 mol) of trimethylsulfonium iodide and 70.4 g (0.50 mol) of o-bromo-benzaldehyde there is obtained o-bromostyrene oxide.

Similarly 2.71 g of N-benzyl-2-chloro-3,4-dimethoxyphenethylamine and 2.33 g (0.015 mol) of o-bromostyrene oxide are reacted in methanol to give N-benzyl-N-[2-(2-chloro-3,4- dimethoxyphenyl)ethyl-2-hydroxy-2-(b 2-bromophenyl)ethylamine. The latter is converted to its hydrochloride, which is dissolved in 90 ml of methanol and hydrogenated over 1 g of 10% palladium-on-carbon in 10 ml of ethyl acetate at room temperature for six hours. The reaction mixture is filtered and evaporated in vacuo to leave N-[2-(2-chloro-3,4-dimethoxyphenyl)ethyl]-2-hydroxy-2-(2-bromophenyl)ethylamine hydrochloride.

Cyclization, methylation and splitting of the 7,8-ethers as in Example 1 gives 6-chloro-1-(2-bromophenyl)-7,8-dihydroxy-3-methyl-2,3,4,5-tetrahydro-1H-3-benzazepine hydrobromide.

Using similar reaction conditions with appropriately substituted styrene oxides gave 6-chloro-1-(3-chlorophenyl)-7,8-dihydroxy-3-methyl-2,3,4,5-tetrahydro-3H-1-benzazepine hydrobromide, m.p. 263°–265°; 6-chloro-7,8-dihydroxy-3-methyl-1-(3-trifluoromethylphenyl)-2,3,4,5-tetrahydro-3H-1-benzazepine hydrobromide, m.p. 264°–266° and 6-chloro-7,8-dihydroxy-3-methyl-1-(3-methylphenyl)-2,3,4,5-tetrahydro-3H-1-benzazepine hydrobromide, m.p. 263°–265°.

EXAMPLE 5

6-Chloro-7,8-dihydroxy-3-methyl-1-phenyl-2,3,4,5-tetrahydro-1H-3-benzazepine hydrobromide (10 g) is dissolved in trifluoroacetic acid and reacted with a stoichiometric amount of acetyl chloride at room temperature. The next day the reaction mixture is evaporated and the residue recrystallized to give the desired diacetoxy derivative as the hydrochloride, m.p. 153°–155°. The 6-bromo congener melts at 224° (dec.) as the hydrobromide, the 6-chloro-3-allyl congener melts at 168°–170° as the hydrochloride.

Substituting other alkanoyl anhydrides or chlorides gives various 7,8-alkanoyl derivatives.

EXAMPLE 6

A 5.20 g sample of 6-bromo-7,8-dihydroxy-1-phenyl-2,3,4,5-tetrahydro-1H-3-benzazepine free base is slurried in 100 ml of 1:1 methanol-acetone. The slurry is stirred under nitrogen and chilled to about 0°. Sodium bicarbonate (1.68 g, 0.020 mol) is added as a solid and to the stirred mixture is added 5.69 g (0.040 mol) of methyl iodide in 60 ml of acetone, dropwise over a two to three hour period. After addition is completed the mixture is allowed to warm to ambient temperature and stirred for about 40 hours. The reaction mixture is filtered and the filtrate is concentrated to yield additional solid. The combined solids are slurried in water to remove inorganic salts, filtered and the solid dried to give 6-bromo-7,8-dihydroxy-3,3-dimethyl-1-phenyl-2,3,4,5-tetrahydro-1H-3-benzazepinium iodide.

EXAMPLE 7

Substituting a stoichiometric quantity of 2-fluoro-3,4-dimethoxyphenethylamine in the synthetic procedures of Example 1 gives 6-fluoro-7,8-dimethoxy-1-phenyl-2,3,4,5-tetrahydro-1H-3-benzazepine. Methylation and hydrolysis with boron tribromide as in Example 1 gives 6-fluoro-7,8-dihydroxy-3-methyl-1-phenyl-2,3,4,5-tetrahydro-1H-3-benzazepine. Substituting 2-trifluoromethyl-3,4-dimethoxyphenethylamine, prepared via 2-trifluoromethyl-3,4-dimethoxytoluene, in Example 1 gives 6-trifluoromethyl-7,8-dimethoxy-1-phenyl-2,3,4,5-tetrahydro-1H-3-benzazepine then methylation and hydrolysis with boron tribromide gives 6-trifluoromethyl-7,8-dihydroxy-3-methyl-1-phenyl-2,3,4,5-tetrahydro-1H-3-benzazepine.

EXAMPLE 8

A mixture of 3.0 g (0.0095 mole) of 6-chloro-7,8-dimethoxy-1-phenyl-2,3,4,5-tetrahydro-1H-3-benzazepine, 5.5 g (0.04 mole) of potassium carbonate and 1.15 g (0.0095 mole) of allyl bromide in 80 ml of dry dimethylformamide was refluxed for 45 minutes, filtered and the filtrate evaporated to dryness. The residue was dissolved in ethyl acetate, washed with water and dried and concentrated to the light yellow oil (2.46 g, 78%). T.l.c. (10% methanol in chloroform) showed no starting material. The crude benzazepine was dissolved in 50 ml of dry methylene chloride and treated dropwise at −15° to −10° with 4.5 g (0.018 mole) of boron tribromide in 25 ml of dry methylene chloride. After being stirred at 0° for 2 hours, then at room temperature for one hour, the reaction was recooled, treated with excess methanol and evaporated to a tan solid. The crude product was dissolved in a little 2-propanol, diluted with ether and chilled to give 1.25 g (52%) of white 3-allyl-6-chloro-7,8-dihydroxy-1-phenyl-2,3,4,5-tetrahydro-1H-3-benzazepine hydrobromide; m.p. 200°–201°.

EXAMPLE 9

To a solution of 2.5 g (7.35 mmole) of the product of Example 1 in 30 ml of trifluoroacetic acid was added dropwise at room temperature 2.2 ml (3.7 g, 30 mmole) of acetyl bromide. The solution was stirred at 25° for 2 hours, evaporated and the residue treated with cold 5% bicarbonate under an ethyl acetate layer. The organic layer was washed with brine, dried and treated with ethered hydrogen chloride to give the white, crystalline 6-chloro-7,8-diacetoxy-3-methyl-1-phenyl-2,3,4,5-tetrahydro-1H-3-benzazepine hydrochloride; m.p. 153°–155° (1.95 g, 63%).

EXAMPLE 10

A mixture of 1.8 g (5.7 mmole) of the 6-chloro-7,8-dimethoxybenzazepine, 1.0 g of potassium hydroxide, 2.4 g (20 mmole) of ethyl bromide and 60 ml of methanol was heated in a steel bowl at 110°–120° for 4 hours. The mixture was concentrated, partitioned between methylene chloride and water and the layers separated. The dried, concentrated organic extract was chromatographed on 60 g of silica gel with a 2 to 6% methanol in chloroform gradient. The homogeneous N-ethyl compound was collected to give 1.2 g (61%) of yellow oil. This was dissolved in 50 ml of dry methylene chloride, cooled to −10° and 2.5 g (0.01 mole) of boron tribromide in 15 ml of methylene chloride was added dropwise. The mixture was stirred at room temperature for 2 hours, recooled and excess methanol was added. After azeotroping with more methanol, the residue was crystallized from acetonitrile to give 0.5 g (37%) of 6-chloro-3-ethyl-7,8-dihydroxy-1-phenyl-2,3,4,5-tetrahydro-1H-3-benzazepine hydrobromide; m.p. 203°–205°.

EXAMPLE 11

| Ingredients | Mg. per Tablet |
|---|---|
| 6-Chloro-7,8-dihydroxy-3-methyl-1-phenyl-2,3,4,5-tetrahydro-1H-3-benzazepine (as an acid addition salt) | 25 (free base) |
| Magnesium stearate | 2 |
| Lactose | 200 |

The above ingredients are thoroughly mixed and placed into hard gelatin capsules. Such capsules are administered orally to subjects in need of treatment from 1–5 times daily to induce dopaminergic activity.

EXAMPLE 12

| Ingredients | Mg. per Tablet |
|---|---|
| 6-Chloro-7,8-dihydroxy-3-methyl-1-phenyl-2,3,4,5-tetrahydro-1H-3-benzazepine (as an acid addition salt) | 100 (free base) |
| Corn Starch | 30 |
| Polyvinyl pyrrolidone | 12 |
| Corn Starch | 16 |
| Magnesium stearate | 3 |

The first two ingredients are thoroughly mixed and granulated. The granules obtained are dried, mixed with the remaining corn starch and magnesium stearate, and compressed into scored tablets which may be broken to give 50 mg tablets.

The capsules or tablets thusly prepared are administered orally to an animal or human requiring stimulation of either central dopamine receptors within the dose ranges set forth hereinabove. Similarly other compounds of Formula I and the illustrative examples can be formulated in the same manner to give pharmaceutical compositions useful in the methods of this invention based on the chemical characteristics and relative biological activity using the test methods outlined.

What is claimed is:

1. A chemical compound of the structural formula:

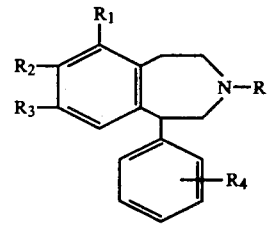

in which:
R is methyl, ethyl or allyl;
$R_1$ is halo or trifluoromethyl;
$R_2$ and $R_3$ are hydroxy or lower alkanoyloxy of 2–7 carbons; and
$R_4$ is hydrogen, methyl, halo, methoxy or trifluoromethyl; or a nontoxic, pharmaceutically acceptable salt thereof.

2. A compound of claim 1 in which $R_4$ is hydrogen.

3. A compound of claim 1 in which $R_4$ is hydrogen and $R_1$ is chloro.

4. The compound of claims 1, 2 or 3 in which R is methyl.

5. The compound of claims 1, 2 or 3 in which $R_2$ and $R_3$ are hydroxy.

6. The compound of claim 1 being 6-chloro-3-methyl-7,8-dihydroxy-1-phenyl-2,3,4,5-tetrahydro-1H-3-benzazepine and its hydrohalide or methane sulfonate salt.

7. The compound of claim 6 in which the salt form is the methane sulfonate.

8. The compound of claim 1 being 6-chloro-3-ethyl-7,8-dihydroxy-1-phenyl-2,3,4,5-tetrahydro-1H-3-benzazepine and its hydrohalide or methane sulfonate salt.

9. The compound of claim 1 being 6-chloro-3-methyl-7,8-diacetoxy-1-phenyl-2,3,4,5-tetrahydro-1H-3-benzazepine and its hydrochloride or methane sulfonate salt.

10. The method of producing central nervous system dopaminergic activity in a subject in need thereof comprising administering to said subject orally or by injection a nontoxic dopaminergic quantity of a compound of claims 1, 3 or 6.

11. The method of claim 10 in which the subject has Parkinson's disease.

12. A pharmaceutical composition having central nervous system dopaminergic activity comprising a nontoxic dopaminergic quantity of a compound of claims 1, 3 or 6 selected from the dosage unit range of from 0.5–400 mg combined with a pharmaceutical carrier.

13. The composition of claim 12 in which the composition is adapted for oral use and the range is from 50–250 mg.

14. The compound of claim 1 being 3-allyl-6-chloro-1-(3-methylphenyl)-7,8-dihydroxy-2,3,4,5-tetrahydro-1H-3-benzazepine or a nontoxic, pharmaceutically acceptable acid addition salt thereof.

* * * * *